(12) United States Patent
Chen et al.

(10) Patent No.: US 8,785,169 B2
(45) Date of Patent: Jul. 22, 2014

(54) CUTINASE-PRODUCING GENETICALLY ENGINEERED MICROORGANISM AND USE THEREOF

(75) Inventors: Jian Chen, Wuxi (CN); Jing Wu, Wuxi (CN); Dan Wu, Wuxi (CN); Lei Wang, Wuxi (CN)

(73) Assignee: Jiangnan University, Wuxi (CN)

( * ) Notice: Subject to any disclaimer, the term of this patent is extended or adjusted under 35 U.S.C. 154(b) by 236 days.

(21) Appl. No.: 13/264,560

(22) PCT Filed: Feb. 28, 2011

(86) PCT No.: PCT/CN2011/000325
§ 371 (c)(1),
(2), (4) Date: Oct. 14, 2011

(87) PCT Pub. No.: WO2012/075662
PCT Pub. Date: Jun. 14, 2012

(65) Prior Publication Data
US 2012/0149086 A1    Jun. 14, 2012

(30) Foreign Application Priority Data
Dec. 8, 2010  (CN) .......................... 2010 1 0578924

(51) Int. Cl.
*C12N 9/18* (2006.01)
*C12N 1/20* (2006.01)
(52) U.S. Cl.
CPC ........... *C12N 9/18* (2013.01); *C12Y 301/01074* (2013.01)
USPC ..................................... 435/197; 435/252.3
(58) Field of Classification Search
USPC ............................................ 435/197, 252.3
See application file for complete search history.

(56) References Cited

FOREIGN PATENT DOCUMENTS

| CN | 101705211 A | 5/2010 |
| CN | 101792729 A | 8/2010 |

OTHER PUBLICATIONS

Written Opinion of the International Searching authority (Jul. 7, 2011).*
Chen et al., "Identificaton and Characterization of Bacterial Cutinase," Journal of Biological Chemistry, Sep. 19, 2008, pp. 25854-25862, vol. 283, No. 38.
Fengzhen et al., "Cutinase Production Conditions with Thermobifida FUSCA," Chinese Journal of Applied Environmental Biology, Oct. 25, 2005, pp. 608-610, 11(5).
Chen et al., "Purification and Characterization of Cutinase from a Thermophilic Bacterium," Chinese Journal of Applied Environmental Biology, Dec. 25, 2009, pp. 846-850, 15(6).
Chen et al., "Biochemical characterization of the cutinases from Thermobifida fusca," Journal of Molecular Catalysis B: Enzymatic, 2010, pp. 121-127, vol. 63.
Chen et al., "Effects of Fed-fermentation on Cutinase Production by Recombinant *Bacillus subtilis*," China Biotechnology, 2010, pp. 62-66, vol. 30, No. 1.

* cited by examiner

*Primary Examiner* — Tekchand Saidha
(74) *Attorney, Agent, or Firm* — The Webb Law Firm

(57) ABSTRACT

The present invention relates to the field of bioengineering and discloses a cutinase-producing genetically engineered microorganism and use thereof. Recombinant plasmid Tfu_0883-hlyAs/pET20b(+) was constructed and transformed into *E. coli* BL21(DE3) to obtain recombinant *E. coli* strain Tfu_0883-hlyAs/pET20b(+)/*E. coli* BL21(DE3). Specific growth rate was maintained at a certain value using fed-batch fermentation mode. After fermenting 30-34 hours, the enzyme activity in the supernatant reached 700-750 U/mL. The present invention uses glycerol as the main raw material and employs semi-synthetic medium, has the advantages of good stability and ease of control, and is suitable for large-scale production.

7 Claims, No Drawings

SEQUENCE LISTING

```
<160> NUMBER OF SEQ ID NOS: 4

<210> SEQ ID NO 1
<211> LENGTH: 30
<212> TYPE: DNA
<213> ORGANISM: Artificial Sequence
<220> FEATURE:
<223> OTHER INFORMATION: Designed based on gene sequence, used for
      amplification

<400> SEQUENCE: 1
gtaatccata tggccaaccc ctacgagcgc                                    30

<210> SEQ ID NO 2
<211> LENGTH: 32
<212> TYPE: DNA
<213> ORGANISM: Artificial Sequence
<220> FEATURE:
<223> OTHER INFORMATION: Designed based on gene sequence, used for
      amplification

<400> SEQUENCE: 2
gacttccata ggctaagaac gggcaggtgg ag                                 32

<210> SEQ ID NO 3
<211> LENGTH: 32
<212> TYPE: DNA
<213> ORGANISM: Artificial Sequence
<220> FEATURE:
<223> OTHER INFORMATION: Designed based on gene sequence, used for
      amplification

<400> SEQUENCE: 3
ctccacctgc ccgttcttag cctatggaag tc                                 32

<210> SEQ ID NO 4
<211> LENGTH: 29
<212> TYPE: DNA
<213> ORGANISM: Artificial Sequence
<220> FEATURE:
<223> OTHER INFORMATION: Designed based on gene sequence, used for
      amplification
```

```
<400> SEQUENCE: 4
ccgctcgagt tatgctgatg ctgtcaaag                                           29
```

CUTINASE-PRODUCING GENETICALLY ENGINEERED MICROORGANISM AND USE THEREOF

TECHNICAL FIELD

The present invention relates to the field of bioengineering, particularly to a cutinase-producing genetically engineered microorganism and use thereof.

BACKGROUND ART

Cutinase is a multifunctional enzyme that belongs to the family of serine esterase. It can not only hydrolyze long- and short-chain fatty acid esters, emulsified triglycerides and soluble synthetic esters, but also participate in esterification, transesterification etc. By virtue of its special structure, cutinase can also hydrolyze cutin. Therefore, cutinase finds wide application in a variety of industries, including textile, food, biocatalysis and chemical industries.

Researches on the fermentation of cutinase are mainly focused on optimization of culturing conditions of wild microorganism strains and highly efficient expression of recombinant fungal cutinase using different genetically engineered host cells (such as *Saccharomyces cerevisiae*, *E. coli*, and *Aspergillus* spp.), aiming to optimize production processes and reducing production cost, among others. However, so far no reports are available on the industrialized production of cutinase, due to the problems of high cost of cultivation and long period of growth of yeasts, as well as poor stability of *F. solani pisi*, a recombinant strain for producing cutinase.

Cheng Sheng from our laboratory reported (Chen S, Tong X, Woodard R W, Du G C, Wu J, Chen J, Identification and Characterization of Bacterial Cutinase, The Journal of Biological Chemistry, 2008, 283 (28) 25854-25862) cutinase from *Thermobifida fusca* which showed a good thermal stability, a wide pH stability range, an optimal temperature of 60° C., and an optimal pH of 8.0, consistent with the requirements of application of cutinase for textile use. Based on this, optimization of fermentation was conducted, achieving an enzyme activity of 500 U/mL in a fermentation run in a 3 L fermentor for 30 hours (Chinese Patent Application No. 200910259651.1 to Jing Wu, Dan Wu, Yao Zhang, Jian Chen, and Sheng Chen, titled "A Fermentation Process of Recombinant Cutinase"). However, two disadvantages remain. Firstly, supplementation on the basis of complex media resulted in complexity of the components and inconvenience in the control of fermentation process. Secondly, use of the type II secretion pathway to transport across the outer and inner membranes of *E. coli* in two steps yielded low efficiency of transport, while addition of a certain amount of glycine during fermentation to modify the permeability of cell wall in order to increase the level of extracellular secretion lead to increased production cost.

SUMMARY OF THE INVENTION

A technical problem to be solved by the present invention is to provide a cutinase-producing genetically engineered microorganism.

The genetically engineered microorganism is a recombinant *E. coli* strain Tfu_0883-hlyAs/pET20b(+)/*E. coli* BL21 (DE3) obtained by constructing recombinant plasmid Tfu_0883-hlyAs/pET20b(+) and transforming the plasmid into *E. coli* BL21(DE3).

The cutinase-producing genetically engineered microorganism is constructed as follows:

1) cutinase Tfu_0883 gene is amplified using plasmid Tfu_0883/pET20b(+) previously constructed in our laboratory as template;
2) hlyAs gene is amplified using *E. coli* CFT073 total DNA as template (Chinese Patent Application No. 200910260984.6);
3) PCR amplification is performed using the PCR fragments of Tfu_0883 gene and hlyAs gene recovered by gel cutting as templates to obtain Tfu_0883-hlyAs gene;
4) pET20b(+) and Tfu_0883-hlyAs are subjected to double enzyme digestion, and the products recovered by gel cutting are transformed into *E. coli* JM109 competent cells to obtain plasmid Tfu_0883-hlyAs/pET20b (+);
5) the recombinant plasmid Tfu_0883-hlyAs/pET20b(+) is transformed into *E. coli* BL21(DE3) to obtain *E. coli* strain Tfu_0883-hlyAs/pET20b(+)/*E. coli* BL21(DE3).

The above-said Tfu_0883/pET20b(+) can be obtained using conventional means (Chen S, Tong X, Woodard R W, Du G C, Wu J, Chen J, Identification and Characterization of Bacterial Cutinase, The Journal of Biological Chemistry, 2008, 283 (28) 25854-25862).

The above-said plasmid pET20b(+) and *E. coli* BL21 (DE3) strain are commercially available from Novagen Inc., and *E. coli* CFT073 strain (ATCC 700928) is available from ATCC.

Another technical problem to be solved by the present invention is to provide a method for the production of cutinase by fermenting the above-said cutinase-producing genetically engineered microorganism.

The above-said problem is addressed by the following specific production processes:

1) during fermentation, the temperature is maintained at 36-38° C., the dissolved oxygen is maintained at 20-40% by increasing or decreasing stirring rotation speed or supplying oxygen-rich air, and the pH is maintained at 7.0-7.2 in the growth stage and at 6.4-6.6 in the stage of induction of production of the enzyme by supplementing ammonia water;
2) after fermenting for 5-6 hours or when the concentration of dissolved oxygen rises to more than 70%, 500 g/L of glycerol is supplemented at an initial flow rate of 3.5-5.0 mL·L$^{-1}$·h$^{-1}$, and subsequently, glycerol is fed in exponential feeding mode to control the specific growth rate of the microorganism in the range of 0.15-0.22 h$^{-1}$;
3) after fermenting for 12-13 hours or when OD$_{600}$ reaches 25-35, IPTG is added at a final concentration of 0.02-0.04 mM/L for induction, and at the same time 50 g/L of lactose is supplemented at a rate of 8-10 mL·L$^{-1}$·h$^{-1}$ and the supplementation of ammonia water is stopped until the pH drops to 6.4-6.6, at which time the supplementation of ammonia water is resumed to control the pH at 6.4-6.6;
4) after fermenting for 15-17 hours or inducing for 3-4 hours, glycerol is fed at a constant flow rate of about 25-35 mL·L$^{-1}$·h$^{-1}$;
5) after fermenting for 19-21 hours or when OD$_{600}$ no longer increases, the flow rate of lactose is decreased to 2-4 mL·L$^{-1}$·h$^{-1}$, and the flow rate of glycerol is gradually decreased to half of that in step 4) over 6-8 hours.

Seed culture is obtained by inoculating the inoculum having been stored at −80° C. in a seed culture medium at an initial pH of 7.0-7.2 and culturing on a constant-temperature rotating shaking bed at 37° C., 200 rpm for 7-8 hours. The seed culture medium consists of 10 g/L of peptone, 5 g/L of yeast powder, 10 g/L of NaCl and 100 mg/L of ampicillin.

The seed culture is inoculated at an amount of 4-8% for the fermentation.

The fermentation medium consists of 1 g/L of peptone, 2 g/L of yeast powder, 4 g/L of $(NH_4)_2HPO_4$, 13.5 g/L of $KH_2PO_4$, 4.1 g/L of $MgSO_4.7H_2O$, 0.85 g/L of citric acid, 8 g/L of glycerol, 5 mL/L of a solution of trace elements and 100 mg/L of ampicillin. The seed culture is inoculated at an amount of 4-8% for the fermentation.

The solution of trace elements consists of 5 M/L of HCl, 10 g/L of $FeSO_4.7H_2O$, 2.25 g/L of $ZnSO_4.7H_2O$, 1.0 g/L of $CuSO_4.5H_2O$, 0.5 g/L of $MnSO_4.4H_2O$, 0.23 g/L of $Na_2B_4O_7.10H_2O$, 2.0 g/L of $CaCl_2.2H_2O$ and 0.1 g/L of $(NH_4)_6Mo_7O_{24}$.

The cutinase-producing genetically engineered microorganism Tfu_0883-hlyAs/pET20b(+)/BL21(DE3) constructed according to the present invention, when cultured in a flask for 60 hours, achieved a yield of cutinase of up to 274 U/mL, and when fermented using the method provided in the present invention for 30-34 hours, achieved an activity of cutinase of 700-750 U/mL. The present invention also has the advantages of low cost of the fermentation medium and easy control over the microorganism, and is adapted for application in the industrialized production of cutinase.

DETAILED DESCRIPTION OF THE INVENTION

The present invention is further described by the following examples, which should be considered as illustrative and not limitative of the scope of the present invention. In the following examples, those experimental procedures for which specific conditions are not specified are essentially performed in accordance with the conditions described in commonly used manuals for molecular cloning.

Strains and plasmid: plasmid pET20b(+), and strains E. coli BL21(DE3), E. coli CFT073 and E. coli JM109.

Materials and methods: restriction endonucleases, T4 DNA ligase, pMD18-T simple vector, PCR reagents and DNA Markers were purchased from Takara Co., Ltd.; competent E. coli JM109 cells, primers, plasmid extraction kit and PCR products purification kit were purchased from Sangon Biotech (Shanghai) Co., Ltd. The electroporator was purchased from Bio-Rad Co., Ltd.

Example 1

Construction of Tfu_0883-hlyAs-pET20b(+)/E. coli BL21 (DE3)

Based on the genes of cutinase and hlyAs, two pairs of primers P1, P2 and P3, P4 were designed.

```
P1: 5'-GTAATCCATATGGCCAACCCCTACGAGCGC-3'

P2: 5'-GACTTCCATAGGCTAAGAACGGGCAGGTGGAG-3'

P3: 5'-CTCCACCTGCCCGTTCTTAGCCTATGGAAGTC-3'

P4: 5'-CCGCTCGAGTTATGCTGATGCTGTCAAAG-3'
```

The gene of cutinase, Tfu_0883, was amplified by PCR using plasmid Tfu_0883/pET20b(+)DNA as template and P1, P2 as primers. The gene of hlyAs was amplified by PCR using E. coli CFT073 total DNA as template and P3, P4 as primers.

The PCR reactions were performed in a 50 μL system under the conditions of: denaturing at 94° C. for 1 minute, and then 30 cycles of denaturing at 94° C. for 30 seconds, annealing at 60° C. for 30 seconds, and elongation at 72° C. for 1 minute and 20 seconds respectively, followed by elongation at 72° C. for 10 minutes. The amplification yielded PCR fragments of 783 bp and 180 bp respectively, which were recovered by gel cutting.

Again, PCR reaction was performed using the PCR fragments of Tfu_0883 gene and hlyAs gene recovered by gel cutting as templates and P1, P4 as primers. The amplification yielded a PCR fragment of 963 bp, which was recovered by gel cutting. The recovered fragment was ligated with pMD18-T simple vector and the ligation product was transformed into E. coli JM109. The transformed cells were plated on an LB solid plate containing 100 mg/L of ampicillin and cultured at 37° C. overnight. Single clones were picked and inoculated into an LB liquid medium containing 100 mg/L of ampicillin and cultured at 37° C., 200 rpm for 8-10 hours followed by extraction of the plasmid. The plasmid was sequenced, indicating that this gene had 963 nucleotides in full length and was completely consistent with the sequences of both Tfu_0883 and hlyAs genes.

The pET20b(+) plasmid and the Tfu_0883-hlyAs gene were subjected to double enzyme digestion with NdeI and XhoI. The enzyme digestion products were recovered by gel cutting and then ligated using T4 ligase at 16° C. overnight. The ligation products were transformed into competent E. coli JM109 cells. The transformed cells were plated on an LB solid plate containing 100 mg/L of ampicillin and cultured at 37° C. overnight. The transformants were picked into an LB liquid medium containing 100 mg/L of ampicillin and cultured, followed by extraction of the plasmid to obtain the enriched Tfu_0883-hlyAs/pET20b(+) plasmid.

The recombinant plasmid Tfu_0883-hlyAs/pET20b(+) was transformed into E. coli BL21 (DE3) host strain. The transformed cells were cultured on an LB plate containing 100 mg/L of ampicillin at 37° C. for 8-10 hours and the transformants (Tfu_0883-hlyAs-pET20b(+)/E. coli BL21 (DE3)) were picked.

Example 2

Shake-flask Fermentation of E. coli Strain Tfu_0883-hlyAs/pET20b(+)/E. coli BL21(DE3)

Strain: E. coli strain Tfu_0883-hlyAs/pET20b(+)/E. coli BL21(DE3).

Seed culture: Inoculum having been stored at −80° C. was inoculated in a seed culture medium at an initial pH of 7.0-7.2 and cultured on a constant-temperature rotating shaking bed at 37° C., 200 rpm for 7-8 hours. The seed culture medium consisted of 10 g/L of peptone, 5 g/L of yeast powder, 10 g/L of NaCl and 100 mg/L of ampicillin.

Fermentation to produce the enzyme: The seed culture was inoculated at an amount of 5% for the fermentation; the fermentation medium consisted of 5 g/L of glycerol, 12 g/L of peptone, 24 g/L of yeast extract, 12.54 g/L of $K_2HPO_4$ and 2.31 g/L of $KH_2PO_4$; after culturing at 37° C. for 2 hours, IPTG was added at a final concentration of 0.4 mM for induction, and culturing was continued at a lowered temperature of 25° C., with the yield of the enzyme reaching 274 U/mL at 60 hours.

Example 3

Fermentation of E. coli Strain Tfu_0883-hlyAs/pET20b(+)/E. coli BL21(DE3)

Strain: E. coli strain Tfu_0883-hlyAs/pET20b(+)/E. coli BL21(DE3).

Seed culture: Inoculum having been stored at −80° C. was inoculated in a seed culture medium at an initial pH of 7.0-7.2 and cultured on a constant-temperature rotating shaking bed at 37° C., 200 rpm for 7-8 hours. The seed culture medium consisted of 10 g/L of peptone, 5 g/L of yeast powder, 10 g/L of NaCl and 100 mg/L of ampicillin.

The seed culture was inoculated at an amount of 4-8% for the fermentation.

The fermentation medium consisted of 1 g/L of peptone, 2 g/L of yeast powder, 4 g/L of $(NH_4)_2HPO_4$, 13.5 g/L of $KH_2PO_4$, 4.1 g/L of $MgSO_4.7H_2O$, 0.85 g/L of citric acid, 8 g/L of glycerol, 5 mL/L of a solution of trace elements and 100 mg/L of ampicillin. The solution of trace elements consisted of 5 M/L of HCl, 10 g/L of $FeSO_4.7H_2O$, 2.25 g/L of $ZnSO_4.7H_2O$, 1.0 g/L of $CuSO_4.5H_2O$, 0.5 g/L of $MnSO_4.4H_2O$, 0.23 g/L of $Na_2B_4O_7.10H_2O$, 2.0 g/L of $CaCl_2.2H_2O$ and 0.1 g/L of $(NH_4)_6Mo_7O_{24}$.

1) during fermentation, the temperature was maintained at 36-38° C., the dissolved oxygen was maintained at 20-40% by increasing or decreasing stirring rotation speed or supplying oxygen-rich air, and the pH was maintained at 7.0-7.2 in the growth stage and at 6.4-6.6 in the stage of induction of production of the enzyme by supplementing ammonia water;

2) after fermenting for 5-6 hours or when the concentration of dissolved oxygen rose to more than 70%, 500 g/L of glycerol was supplemented at an initial flow rate of 3.5-5.0 $mL \cdot L^{-1} \cdot h^{-1}$, and subsequently, glycerol was fed in exponential feeding mode to control the specific growth rate of the microorganism in the range of 0.15-0.22 $h^{-1}$;

3) after fermenting for 12-13 hours or when $OD_{600}$ reached 25-35, IPTG was added at a final concentration of 0.02-0.04 mM/L for induction, and at the same time 50 g/L of lactose was supplemented at a rate of 8-10 $mL \cdot L^{-1} \cdot h^{-1}$ and the supplementation of ammonia water was stopped until the pH dropped to 6.4-6.6, at which time the supplementation of ammonia water was resumed to control the pH at 6.4-6.6;

4) after fermenting for 15-17 hours or inducing for 3-4 hours, glycerol was fed at a constant flow rate of 25-35 $mL \cdot L^{-1} \cdot h^{-1}$;

5) after fermenting for 19-21 hours or when $OD_{600}$ no longer increased, the flow rate of lactose was decreased to 2-4 $mL \cdot L^{-1} \cdot h^{-1}$, and the flow rate of glycerol was gradually decreased to half of that in step 4) over 6-8 hours.

When fermenting for 30-34 hours, the enzyme activity reached 700-750 U/mL.

The invention claimed is:

1. A cutinase-producing genetically engineered microorganism, comprising cutinase Tfu_0883 gene and hlyAs gene introduced into *E. coli*.

2. A cutinase-producing genetically engineered microorganism, wherein the genetically engineered microorganism is *E. coli* BL21 (DE3) carrying recombinant plasmid Tfu_0883-hlyAs/pET20b(+).

3. The genetically engineered microorganism according to claim 1, wherein the genetically engineered microorganism is constructed as follows:
 1) cutinase Tfu_0883 gene is amplified using plasmid Tfu_0883/pET20b(+) as template;
 2) hlyAs gene is amplified using *E. coli* CFT073 total DNA as template;
 3) PCR amplification is performed using the PCR fragments of Tfu_0883 gene and hlyAs gene recovered by gel cutting as templates to obtain Tfu_0883-hlyAs gene;
 4) pET20b(+) and Tfu_0883-hlyAs are subjected to double enzyme digestion, and the products recovered by gel cutting are transformed into *E. coli* JM109 competent cells to obtain plasmid Tfu_0883-hlyAs/pET20b(+);
 5) the recombinant plasmid Tfu_0883-hlyAs/pET20b(+) is transformed into *E. coli* BL21(DE3) to obtain *E. coli* strain Tfu_0883-hlyAs/pET20b(+)/*E. coli* BL21(DE3).

4. A method for producing cutinase from the genetically engineered microorganism according to claim 1, said method comprising the following steps:
 1) during fermentation, the temperature of the fermentation medium or seed culture medium is maintained at 36-38° C., the dissolved oxygen is maintained at 20-40% by increasing or decreasing stirring rotation speed or supplying oxygen-rich air, and the pH is maintained at 7.0-7.2 in the growth stage and at 6.4-6.6 in the stage of induction of production of the enzyme by supplementing ammonia water;
 2) after fermenting for 5-6 hours or when the concentration of dissolved oxygen rises to more than 70%, 500 g/L of glycerol is supplemented at an initial flow rate of 3.5-5.0 $mL \cdot L^{-1} \cdot h^{-1}$, and subsequently, glycerol is fed in exponential feeding mode to control the specific growth rate of the microorganism in the range of 0.15-0.3 $h^{-1}$;
 3) after fermenting for 12-13 hours or when $OD_{600}$ reaches 25-35, IPTG is added at a final concentration of 0.02-0.04 mM/L for induction, and at the same time 50 g/L of lactose is supplemented at a rate of 8-10 $mL \cdot L^{-1} \cdot h^{-1}$ and the supplementation of ammonia water is stopped until the pH drops to 6.4-6.6, at which time the supplementation of ammonia water is resumed to control the pH at 6.4-6.6;
 4) after fermenting for 15-17 hours or inducing for 3-4 hours, glycerol is fed at a constant flow rate of 25-35 $mL \cdot L^{-1} \cdot h^{-1}$;
 5) after fermenting for 19-21 hours or when $OD_{600}$ no longer increases, the flow rate of lactose is decreased to 2-4 $mL \cdot L^{-1} \cdot h^{-1}$, and the flow rate of glycerol is gradually decreased to half of that in step 4) over 6-8 hours.

5. The method according to claim 4, wherein the seed culture medium or fermentation medium consists of 10 g/L of peptone, 5 g/L of yeast powder, 10 g/L of NaCl and 100 mg/L of ampicillin.

6. The method according to claim 5, wherein the fermentation medium consists of 1 g/L of peptone, 2 g/L of yeast powder, 4 g/L of $(NH_4)_2HPO_4$, 13.5 g/L of $KH_2PO_4$, 4.1 g/L of $MgSO_4 \cdot 7H_2O$, 0.85 g/L of citric acid, 8 g/L of glycerol, 5 mL/L of a solution of trace elements and 100 mg/L of ampicillin.

7. The method according to claim 6, wherein the solution of trace elements consists of 5 M/L of HCl, 10 g/L of $FeSO_4 \cdot 7H_2O$, 2.25 g/L of $ZnSO_4 \cdot 7H_2O$, 1.0 g/L of $CuSO_4 \cdot 5H_2O$, 0.5 g/L of $MnSO_4 \cdot 4H_2O$, 0.23 g/L of $Na_2B_4O_7 \cdot 10H_2O$, 2.0 g/L of $CaCl_2 \cdot 2H_2O$ and 0.1 g/L of $(NH_4)_6Mo_7O_{24}$.

* * * * *